US009315855B2

(12) United States Patent  (10) Patent No.: US 9,315,855 B2
Gheorghiu et al.  (45) Date of Patent: Apr. 19, 2016

(54) SYSTEMS AND METHODS FOR DETECTION AND QUANTITATION OF ANALYTES USING AN OSCILLATING STIMULUS

(75) Inventors: Eugen Gheorghiu, Bucharest (RO); Mihai Sorin David, Bucharest (RO); Cristina Polonschii, Bucharest (RO); Dumitru Bratu, Bucharest (RO)

(73) Assignee: Centrul International De Biodinamica, Bucharest (RO)

( * ) Notice: Subject to any disclaimer, the term of this patent is extended or adjusted under 35 U.S.C. 154(b) by 1100 days.

(21) Appl. No.: 13/398,472

(22) Filed: Feb. 16, 2012

(65) Prior Publication Data

US 2012/0208283 A1  Aug. 16, 2012

(51) Int. Cl.

| | |
|---|---|
| *G01N 27/02* | (2006.01) |
| *C12Q 1/68* | (2006.01) |
| *G01N 21/17* | (2006.01) |
| *G01N 21/552* | (2014.01) |
| *G01N 21/64* | (2006.01) |
| *G01N 33/53* | (2006.01) |
| *G01N 33/543* | (2006.01) |
| *G01N 35/00* | (2006.01) |
| *G01N 27/74* | (2006.01) |

(52) U.S. Cl.
CPC .......... *C12Q 1/6825* (2013.01); *G01N 21/1717* (2013.01); *G01N 21/553* (2013.01); *G01N 21/645* (2013.01); *G01N 27/745* (2013.01); *G01N 33/5308* (2013.01); *G01N 33/5438* (2013.01); *G01N 35/0098* (2013.01); *G01N 27/02* (2013.01); *Y10T 436/143333* (2015.01)

(58) Field of Classification Search
CPC .................................................. G01N 27/02
USPC .......................................................... 436/94
See application file for complete search history.

(56) References Cited

U.S. PATENT DOCUMENTS 5,216,483 A * 6/1993 Berthold et al. .............. 356/318
5,238,815 A   8/1993 Higo et al.
(Continued)

FOREIGN PATENT DOCUMENTS

| EP | 1729112 A1 | 12/2006 |
|---|---|---|
| WO | 2004041061 A2 | 5/2004 |
| WO | 2012141605 A1 | 10/2012 |

OTHER PUBLICATIONS

Rapoport et al. "Integrated Capture, Transport, and Magneto-Mechanical Resonant Sensing of Superparamagnetic Microbeads Using Magnetic Domain Walls," Lab on a Chip, 12(21): p. 4433-4440, Royal Society of Chemestry, London UK; Nov. 2012.

(Continued)

*Primary Examiner* — Christopher A Hixson
*Assistant Examiner* — Emily Berkeley
(74) *Attorney, Agent, or Firm* — Law Office of Andrei D Popovici, PC (57) ABSTRACT

Described systems and methods allow the detection of and determination of a concentration of a target analyte such as a biological cell, a virus, a polypeptide, a toxin, a pesticide, a drug, a drug residue, or a DNA strand, in a fluid sample. A variable stimulus, such as an oscillating magnetic field or a light beam of oscillating intensity, is applied to the sample, inducing variations in a position or shape of a constituent of the sample, or variations in a fluorescence of the sample. Such variations produce measurable variations in electric and/or optical properties of a sensor, variations which allow the determination of the concentration of the target analyte.

22 Claims, 9 Drawing Sheets

(56) References Cited

U.S. PATENT DOCUMENTS

| | | | |
|---|---|---|---|
| 5,641,640 | A | 6/1997 | Hanning |
| 6,437,551 | B1 | 8/2002 | Krulevitch et al. |
| 6,703,819 | B2 * | 3/2004 | Gascoyne et al. ............ 324/71.4 |
| 6,764,583 | B2 | 7/2004 | Miles |
| 7,678,256 | B2 | 3/2010 | Crocker et al. |
| 7,704,363 | B2 * | 4/2010 | Bryning et al. ............... 204/547 |
| 7,718,355 | B2 | 5/2010 | Sim et al. |
| 2001/0053535 | A1 * | 12/2001 | Bashir et al. ..................... 435/34 |
| 2002/0076690 | A1 | 6/2002 | Fuller et al. |
| 2005/0213374 | A1 | 9/2005 | Xu et al. |
| 2006/0008924 | A1 * | 1/2006 | Anker et al. .................. 436/526 |
| 2008/0252305 | A1 * | 10/2008 | Manneschi .................. 324/693 |
| 2010/0075340 | A1 | 3/2010 | Davis et al. |
| 2010/0133118 | A1 * | 6/2010 | Sosnowski et al. ........ 205/777.5 |
| 2011/0009817 | A1 * | 1/2011 | Bennett et al. ............. 604/93.01 |

OTHER PUBLICATIONS

International Search Report and Written Opinion, PCT/RO2012/000003, Applicant: Centrul IntErnational de Biodinamica, p. 1-7, Form PCT/ISA/210 and 220, Sep. 20, 2012

Yang et al., "Magnetically Enhanced High-Specificity Virus Detection Using Bio-activated Magnetic Nanoparticles with Antibodies as Labeling Markers.," Journal of Virological Methods, vol. 164(1-2): p. 14-18, Elsevier B.V., Amsterdam Netherlands; Mar. 2010.

Lin et al., "Detection of Pathogen *Escherichia Coli* O157:H7 with a Wireless Magnetoelastic-Sensing Device Amplified by Using Chitosan-Modified Magnetic Fe3O4 Nanoparticles," Sensors and Actuators B: Chemical, 147(1): p. 343-349, Elsevier B.V., Amsterdam Netherlands; May 18, 2010.

Moser, "Dynamic Actuation of Magnetic Beads for Immunoassays on-chip," Faculte Sciences et Techniques de L'ingenieur, Laboratoire de Microsystemes 2, Programme Doctoral en Microsystemes et Microelectronique, Thesis No. 4691, p. 1-154, Swiss Federal Institute of Technology in Lausanne, Lausanne, Switzerland; May 12, 2010.

Moser et al., "On-Chip Immuno-Agglutination Assay with Analyte Capture by Dynamic Manipulation of Superparamagnetic Beads," Lab on a Chip, 9(22): p. 3261-3267, Royal Society of Chemestry, London UK; Nov. 21, 2009.

Ma et al., "Rapid and Sensitive Detection of Microcystin by Immunosensor based on Nuclear Magnetic Resonance.," Biosensors and Bioelectronics, 25(1), p. 240-243, Elsevier B.V., Amsterdam Netherlands; Sep. 15, 2009.

Moser et al., "Quadrupolar Magnetic Actuation of Superparamagnetic Particles for Enhanced Microfluidic Perfusion," Applied Physics Letters, 94(2): p. 022505-1-022505-3, American Institute of Physics, Melville, NY; Jan. 2009.

Stromberg et al."Sensitive Molecular Diagnostics Using Volume-Amplified Magnetic Nanobeads," Nano Letters, 8 (3): p. 816-821, American Chemical Society, Washington, DC; Jan. 2, 2008.

Hong et al., "Magnetic Susceptibility Reduction Method for Magnetically Labeled Immunoassay," Applied Physics Letters, 88(21): p. 212512-1-212512-3, American Institute of Physics, Melville, NY; May 26, 2006.

Mauriz et al., "Determination of Environmental Organic Pollutants with a Portable Optical Immunosensor," Talanta: The International Journal of Pure and Applied Analytical Chemistry, 69(2): p. 359-364, Elsevier B.V., Amsterdam Netherlands; Apr. 15, 2006.

Kawazumi et al., "Compact Surface Plasmon Resonance (SPR) Immunosensor Using Multichannel for Simultaneous Detection of Small Molecule Compounds," Sensors and Actuators B Chemical: IMCS-10 '04 Proceedings of the Tenth International Meeting on Chemical Sensors, 108(1-2): p. 791-196, Elsevier B.V., Amsterdam Netherlands; Jul. 22, 2005.

Gheorghiu et al., "Assessment of pathogenic bacteria using periodic actuation," Lab on a Chip: Miniaturisataion for chemistry, physics, biology, materials science and bioengineering, 13(16): p. 3139-3294, Royal Society of Chemistry Publishing, London; Aug. 21, 2013.

* cited by examiner

FIG. 12

SYSTEMS AND METHODS FOR DETECTION AND QUANTITATION OF ANALYTES USING AN OSCILLATING STIMULUS

CROSS-REFERENCE TO RELATED APPLICATIONS

This application claims priority to Romanian patent application Ser. A 2011/00135, filed Feb. 16, 2011, and to Romanian patent application Ser. A 2011/00136, filed Feb. 16, 2011, which are incorporated herein by reference.

BACKGROUND

The invention relates to methods and systems for detecting the presence and/or determining the concentration of analytes in fluid samples, and in particular to biosensing and immunoassay systems and methods.

Methods of detecting the presence of and determining the concentration of an analyte in solution using principles of receptor-ligand interactions have been receiving attention worldwide. Such methods may have the sensitivities and specificities required by applications in medicine, as well as in the food and pharmaceutical industries. Target analytes of particular interest comprise biological cells such as bacteria, and also analytes of comparatively lower molecular weight such as and viruses, toxins, and DNA fragments.

For example, US patent application number 20020076690 describes devices and methods for detecting the attachment of pathogens to immobilized antibodies in an electric field by measuring impedance change between adjacent electrodes caused by the presence of the pathogens. U.S. Pat. No. 6,764,583 shows a device used to detect the presence of pathogens on electrodes used to concentrate a sample using the dielectrophoretic force by impedance measurements between the electrodes. In yet another example, U.S. Pat. No. 5,641,640 shows a method for assaying for an analyte in a fluid sample by determining the change in refractive index at a solid optical surface in contact with the sample, caused by the analyte influencing the binding of a species to the optical surface.

Conventional methods and devices using impedance or optical measurements to detect the presence of pathogens may have several disadvantages. Sensor surfaces are commonly functionalized for a specific analyte, which means that a distinct sensor must be used for each kind of analyte. The bio-active coating of such surfaces may also de-activate relatively fast, so each sensor can only be used for a limited number of measurements. Another limitation of conventional methods resides in their limited sensitivity. Such methods detect differences in the electrochemical impedance or refractive index of a sensor between a state in which the analyte is bound to the sensor and a state in which the sensor surface is free of analytes, and such differences are typically very small.

SUMMARY

According to one aspect, a method comprises: applying an oscillating magnetic field to a sample contained in a measurement chamber, the measurement chamber including an electrode pair, the sample comprising a target analyte, and wherein the applied field oscillates with a first frequency; measuring an electrical impedance of the electrode pair, the electrical impedance being indicative of a change of position of the target analyte in response to applying the oscillating magnetic field, wherein measuring the electrical impedance comprises applying an electrical signal to the electrode pair, the electrical signal oscillating with a second frequency distinct from the first frequency; determining a frequency component of the electrical impedance of the electrode pair at the first frequency; and determining a concentration of the target analyte in the sample according to the frequency component of the electrical impedance at the first frequency.

According to another aspect, a system comprises: an electrode pair in contact to a sample comprising a target analyte; a sample actuator configured to apply an oscillating magnetic field to the sample, the magnetic field oscillating with a first frequency; an electrical impedance analyzer configured to measure an electrical impedance of the electrode pair, the electrical impedance indicative of a change of position of the target analyte in response to applying the oscillating magnetic field, wherein measuring the electrical impedance comprises applying an electrical signal to the electrode pair, the electrical signal oscillating with a second frequency distinct from the first frequency; and a computer system configured to determine a frequency component of the electrical impedance of the electrode pair at the first frequency, and to determine a concentration of the target analyte in the sample according to the frequency component of the electrical impedance at the first frequency.

According to another aspect, a method comprises: bringing into contact an electrode pair with a first sample comprising a target analyte, wherein a selected electrode of the electrode pair comprises a set of active sites configured to bind to the target analyte; in response to bringing into contact the electrode pair with the first sample, bringing into contact the electrode pair with a second sample comprising a set of magnetic beads configured to bind to the active sites; applying an oscillating magnetic field to the electrode pair, the magnetic field oscillating with a first frequency; measuring an electrical impedance of the electrode pair, the impedance indicative of a change of position of a subset of the set of magnetic beads in response to applying the oscillating magnetic field, wherein each bead of the subset is bound to an active site of the set of active sites, and wherein measuring the electrical impedance comprises applying an electrical signal to the electrode pair, the electrical signal oscillating with a second frequency distinct from the first frequency; determining a frequency component of the electrical impedance of the electrode pair at the first frequency; and determining a concentration of the target analyte in the sample according to the frequency component of the target electrical impedance at the first frequency.

According to another aspect, a method comprises: applying an oscillating magnetic field to a sample comprising a target analyte, the applied field oscillating with an actuation frequency; illuminating the sample with a light beam; employing a photodetector to determine an intensity of light received from the sample in response to illuminating the sample, the intensity of light being indicative of a change of position of the target analyte in response to applying the oscillating magnetic field; determining a frequency component of the intensity of light at the actuation frequency; and determining a concentration of the target analyte in the sample according to the frequency component of the intensity of light at the actuation frequency.

According to another aspect, a method comprises: illuminating a sample with a light beam, the sample comprising a target analyte, the intensity of the light beam oscillating with an actuation frequency; employing a photodetector to measure an intensity of fluorescent light emitted by the target analyte or by a fluorescent marker attached to the target analyte, in response to illuminating the sample; determining a frequency component of the intensity of fluorescent light at the actuation frequency; and determining a concentration of the target analyte in the sample according to the frequency component of the intensity of fluorescent light at the actuation frequency.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself.

The following description illustrates embodiments of the invention by way of example and not necessarily by way of limitation.

Figure 1:
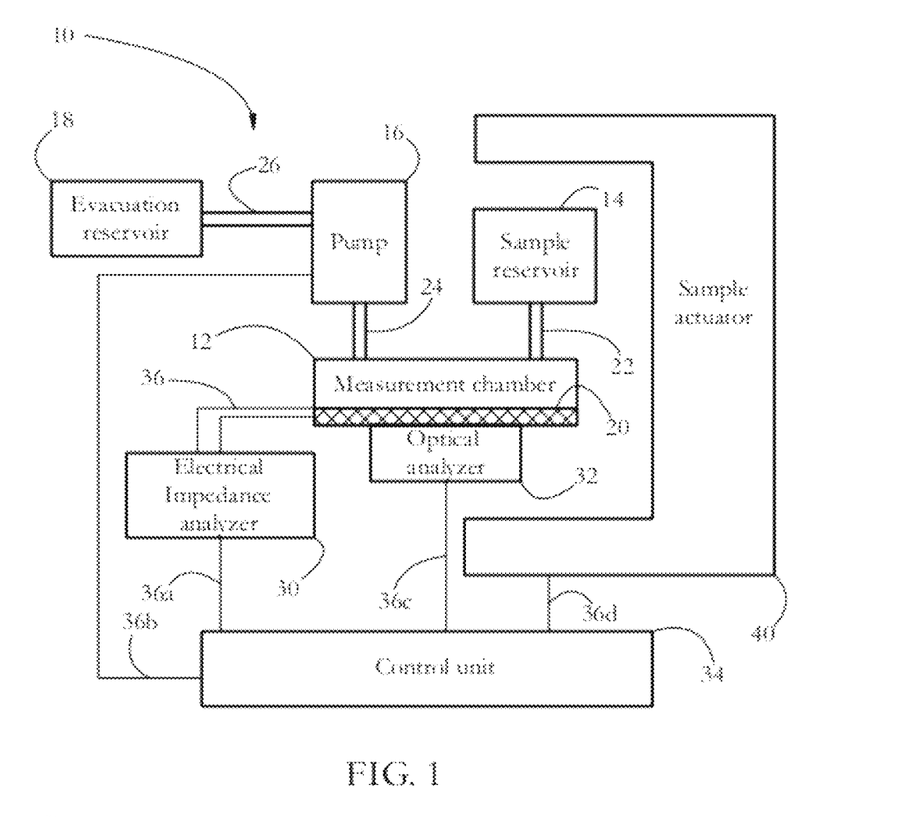
FIG. 1 shows a diagram of an exemplary system for determining a concentration of a target analyte, according to some embodiments of the present invention.

FIG. 1 shows a diagram of an exemplary system for determining a concentration of a target analyte according to some embodiments of the present invention. System 10 comprises a measurement chamber 12 connected to a pump 16 through an evacuation tube 24, and to a sample reservoir 14 through an intake tube 22. Pump 16 is further connected to an evacuation reservoir 18. Measurement chamber 12 includes a sensor 20 connected to an Electrical Impedance (EI) analyzer 30 and an optical analyzer 32.

In some embodiments, system 10 further comprises a sample actuator 40 configured to apply a variable physical stimulus inside measurement chamber 12, as shown below. Pump 16, EI analyzer 30, optical analyzer 32, and sample actuator 40 are connected to a control unit 34 via communication lines 36a-d. In some embodiments, control unit 34 may be a computer system configured to control the operation of items 16 and 40, to receive data from EI analyzer 30 and optical analyzer 32, and to determine a concentration of the target analyte in the sample, among others.

Figure 2:
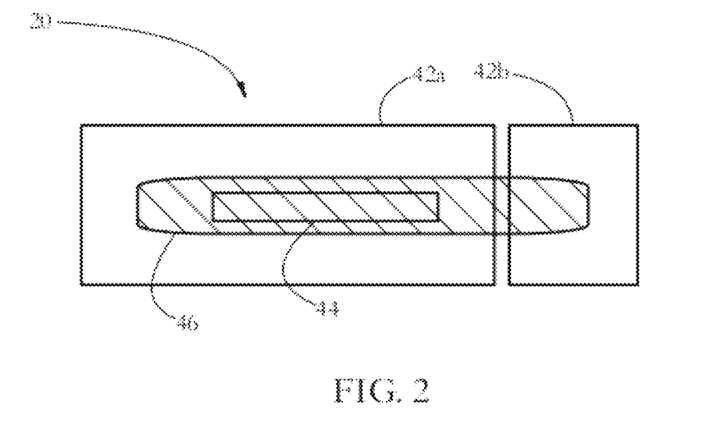
FIG. 2 shows a top view of an exemplary sensor forming part of the measurement chamber of FIG. 1, according to some embodiments of the present invention.

FIG. 2 shows a diagram of an exemplary sensor according to some embodiments of the present invention. In some embodiments, sensor 20 allows a determination of a variation of a physical property such as impedance and/or refractive index of the sensor surface, a variation induced by the presence of the target analyte within the measurement chamber. Sensor 20 comprises a glass substrate covered in a metallic film patterned to form an electrode pair 42a-b, comprising an upper electrode 42a and a lower electrode 42b. In some embodiments, the glass substrate further comprises an optical measurement area 44 acting as a window for optical analyzer 32, and a fluid measurement area 46. Sensor 20 may be passivated by application of a thin layer of inert material. In some embodiments, passivation comprises applying a treatment to sensor 20, such as a chemical substance, which prevents a target analyte in the sample from attaching to the surface of sensor 20. In some embodiments, optical measurement area 44 and upper electrode 42a have substantial overlap. Having both optical and EI probes within a common fluid measurement area 46 yields potential advantages, such as the ability to continuously monitor the quality of the sensor surface and other parameters of the measurement chamber via optical measurements occurring simultaneously with electrical impedance measurements. An exemplary sensor 20 comprises a 0.3 mm thick glass slab, covered with a 50 nm gold layer patterned to produce electrode pair 42a-b, and passivated by e.g. thiolysis (e.g., immersing for 48 hours in a solution of 11-mercapto-undecanol).

Figure 3:
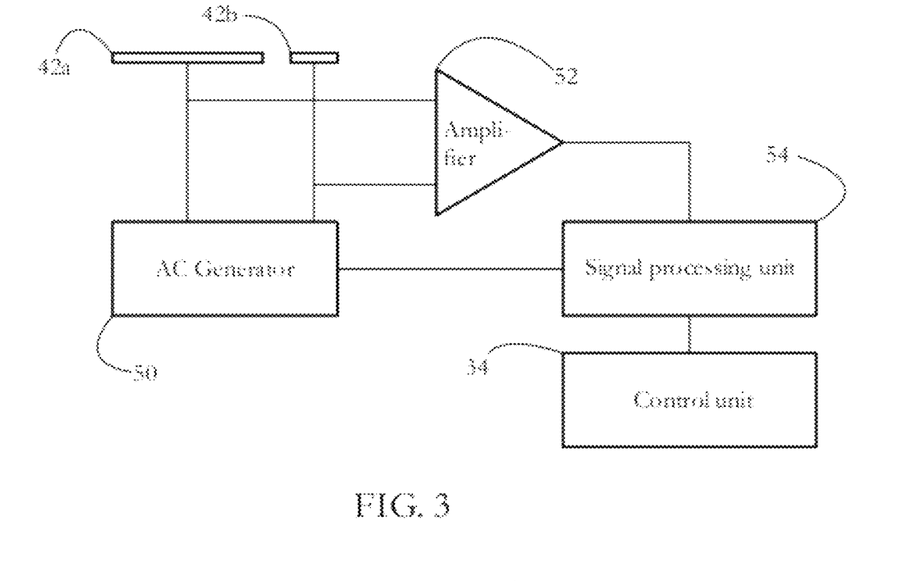
FIG. 3 illustrates an exemplary electrochemical impedance unit according to some embodiments of the present invention.

FIG. 3 shows a diagram of an exemplary EI analyzer 30 according to some embodiments of the present invention. EI analyzer includes an AC generator 50 configured to produce an oscillating electrical signal, an amplifier 52 configured to amplify and/or filter the electrical signal produced by generator 50, and a signal processing unit 54. In some embodiments, AC generator 50 produces a sinusoidal voltage with a range of amplitudes, e.g., 20 µV-2 mV, and a range of frequencies, such as 50 kHz or 500 kHz, which is applied to electrodes 42a-b of sensor 20. Changes in the impedance of electrodes 42a-b, caused by the application of an oscillating magnetic field as shown below, produce a signal which may be measured continuously between electrodes 42a-b. The signal is amplified and/or filtered by amplifier 52 and fed into signal processing unit 54. In some embodiments, signal processing unit 54 is configured to receive a signal from amplifier 52, convert the signal into a digital form, and transmit the digital form to control unit 34, e.g. through a serial communication interface.

Figure 4:
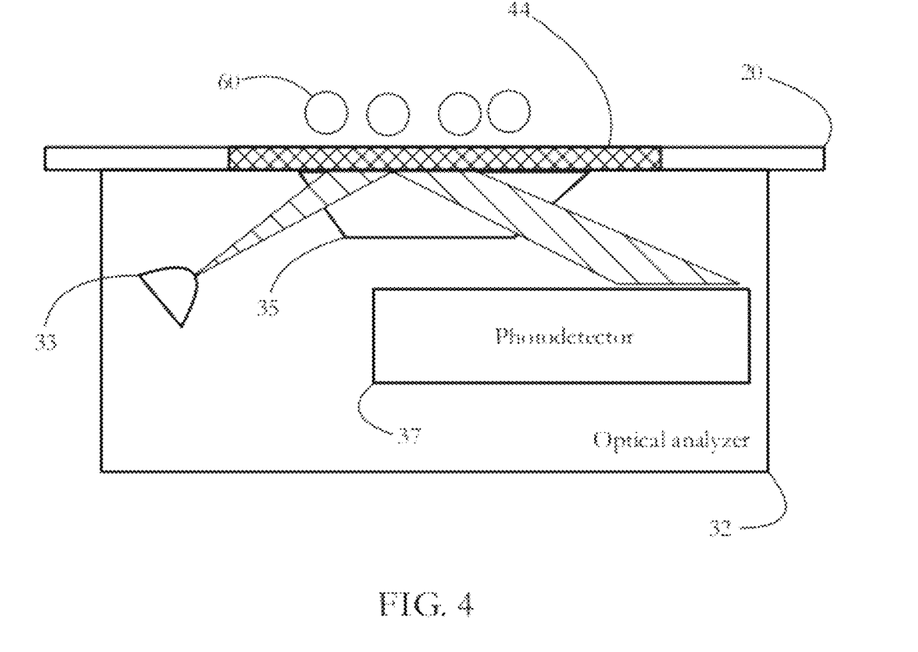
FIG. 4 shows a diagram of an exemplary optical analyzer according to some embodiments of the present invention.

FIG. 4 shows a diagram of an exemplary optical analyzer. In some embodiments, optical analyzer 32 is a Surface Plasmon Resonance (SPR) optical analyzer, comprising a polarized light source 33 such as an LED array, a transparent prism 35, and a photodetector 37. Optical analyzer 32 is configured to determine a value of the refractive index of a layer of the sample in contact with optical measurement area 44 of sensor 20. In some embodiments, optical analyzer 32 is structured according to a Kretschmann prism configuration, wherein the surface of sensor 20 is illuminated by light source 33 at a plurality of predetermined incidence angles, and the intensity of the reflected light is measured by photodetector 37. The incidence angle producing a resonant coupling between the incident light and the surface plasmons of the metallic film covering optical measurement area 44 is known as the SPR angle, and corresponds to a minimum in the intensity of the reflected light. The SPR angle is indicative of the optical properties, such as the refractive index, of a thin layer of sample in contact to the sensor surface. In some embodiments, the SPR angle is recorded, converted into digital form and transmitted to control unit 34. An exemplary optical analyzer 32 comprises a TSPR1K23 device from Texas Instruments, wherein sensor 20 sits on top of prism 35, and wherein the optical contact between prism 35 and sensor 20 is achieved through a thin layer of oil with an index of refraction chosen so as to minimize the deviation of the incident light.

Figure 5:
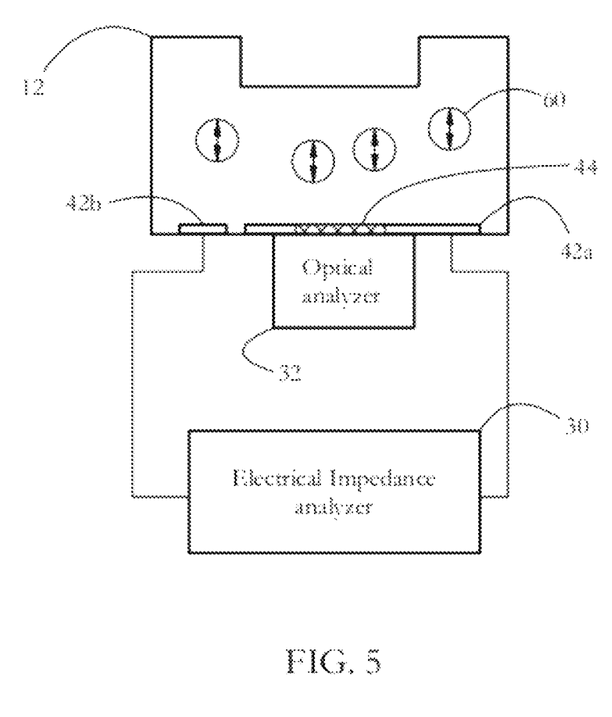
FIG. 5 shows an exemplary measurement chamber connected to an exemplary optical analyzer and electrical impedance analyzer, according to some embodiments of the present invention.

FIG. 5 shows further details of an exemplary measurement chamber 12. In some embodiments, measurement chamber 12 is a sealed cavity, e.g. of prismatic shape, having sensor 20 as a base and two openings at opposite ends, receiving tubes 22 and 24. In an exemplary configuration, tubes 22 and 24 are made of polytetrafluoroethylene (PTFE) and have an internal diameter of 0.5 mm. An exemplary pump 16 comprises a 2 mL syringe, and ensures a flow rate ranging from 0.00625 to 50.0 mL/min. An exemplary measurement chamber further comprises a silicone rubber seal, e.g. 100 µm in thickness, placed on the surface of the sensor. The seal may be pressed onto a biochemically-inert plastic (e.g. polyether-ether-ketone) wall to form a cavity comprising fluid measurement area 46. Such an exemplary area 46 measures 15 mm by 1 mm by 100 µm.

Chamber 12 is configured to receive a sample comprising a target analyte 60. In some embodiments, target analyte 60 may comprise biological cells such as bacteria. Cells may be attached to magnetic particles as shown below, to form complexes or clusters having magnetic properties. In some embodiments, the sample may comprise small target analytes 60 such as viruses or toxins, among others. Some target analytes 60 may comprise DNA fragments, as shown below. In some embodiments, the sample comprises a suspension of magnetic particles such as super-paramagnetic beads, which may attach to the target analyte or to the sensor surface as shown below. In some embodiments, the application of an oscillating magnetic field within the measurement chamber determines oscillations in the position or shape of either the target analyte or magnetic particles. The amplitude of such oscillations may be related to the magnetic properties and/or to the size of the respective particles. Such oscillations may determine a variation in the amplitude of the AC signal between electrodes 42a-b, which may be detected by EI analyzer 30 and transmitted to control unit 34.

Sample actuator 40 comprises a device configured to apply a variable physical stimulus to the sample, the stimulus producing a measurable variation of a physical property, such as a motion, or a change in shape, or a fluorescence, of a constituent of the sample. Stimuli may be magnetic, optical, electrical, or mechanical, among others. For simplicity, the following discussion will focus on a sample actuator 40 configured to deliver a magnetic stimulus in the form of an oscillating magnetic field to measurement chamber. In some embodiments, such an oscillating magnetic field may produce a displacement an/or a change of shape of an indicator particle and/or of a target analyte. Properties of the oscillating magnetic field, such as intensity, time profile, and frequency of oscillation, may be adjustable by a user.

An exemplary embodiment of actuator 40 comprises two magnets: a superior magnet placed substantially above measurement chamber 12, and an inferior magnet placed substantially below chamber 12. The two magnets may include permanent magnets, e.g., NdFeB alloy cubes measuring 5 mm in size, having a remanent magnetic induction of 1 T. Each magnet may be connected to a stepper motor by a rod transforming rotational motion into linear motion. A magnet may thus be moved in an oscillatory fashion, the motion controlled by control unit 34, and producing a magnetic field of oscillating intensity within measurement chamber 12. In an exemplary embodiment, the inferior magnet may produce a constant magnetic field with a gradient substantially perpendicular to sensor 20. A periodic displacement of the superior magnet along a direction substantially perpendicular to sensor 20 produces a magnetic field with a gradient variable in time. The frequency and time-profile of the intensity of the gradient may be chosen by a user according to particularities of the target analyte.

FIG. 5 shows an exemplary variation in a position of a permanent magnet, producing an oscillating magnetic field within the measurement chamber according to some embodiments of the present invention. The superior magnet is kept at a distance $Z_2$ with respect to the sensor surface for a time interval a. Then, within a time interval b, the superior magnet is moved by actuating the stepper motor to a position a distance $Z_1$ away from to the sensor, and subsequently held at distance $Z_1$ for a time interval a. Then the superior magnet is moved back to the initial position a distance $Z_2$ away from the sensor. The cycle is then repeated to produce a periodic oscillation. Exemplary values $Z_2$=34 mm, a=1200 ms, $Z_1$=12 mm, b=877 ms produce a magnetic field oscillating at a frequency of 0.24 Hz. In an experiment, this frequency was found to maximize the amplitude of oscillation of super-paramagnetic 0.5 µm beads within measurement chamber 12. Stepper motors determining the displacement of the superior magnet as shown in FIG. 5 are controlled by control unit 34.

Figure 6:
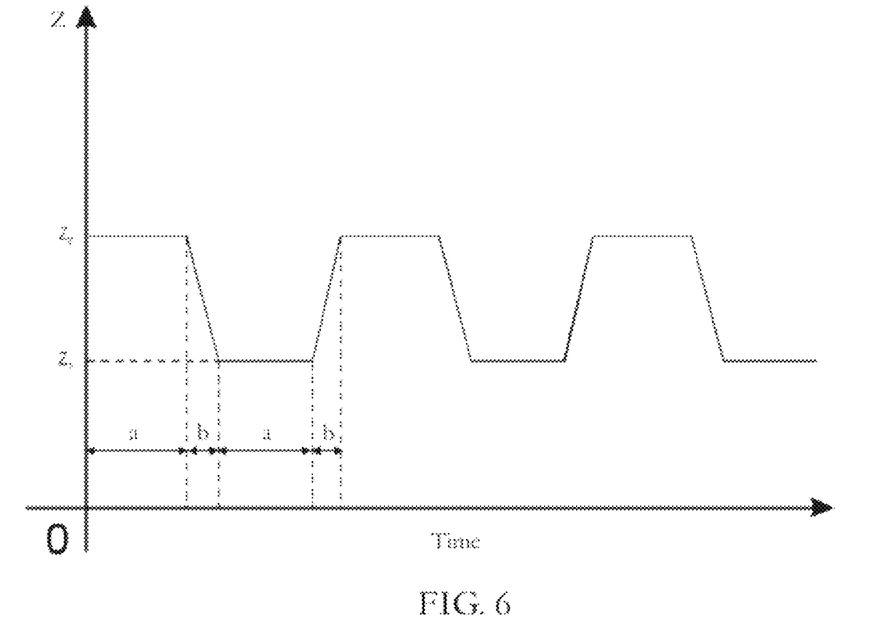
FIG. 6 shows an exemplary oscillation of a position of a magnet, the oscillation producing an oscillating magnetic field within the measurement chamber according to some embodiments of the present invention.

FIG. 6 shows exemplary oscillations in the amplitude of the impedance of electrode pair 42a-b, caused by oscillations in the positions of a suspension of magnetic particles, oscillations induced by an oscillating magnetic field as described above. FIG. 6 shows that the amplitude of impedance oscillations may vary with the size of the analyzed particles.

Figure 7:
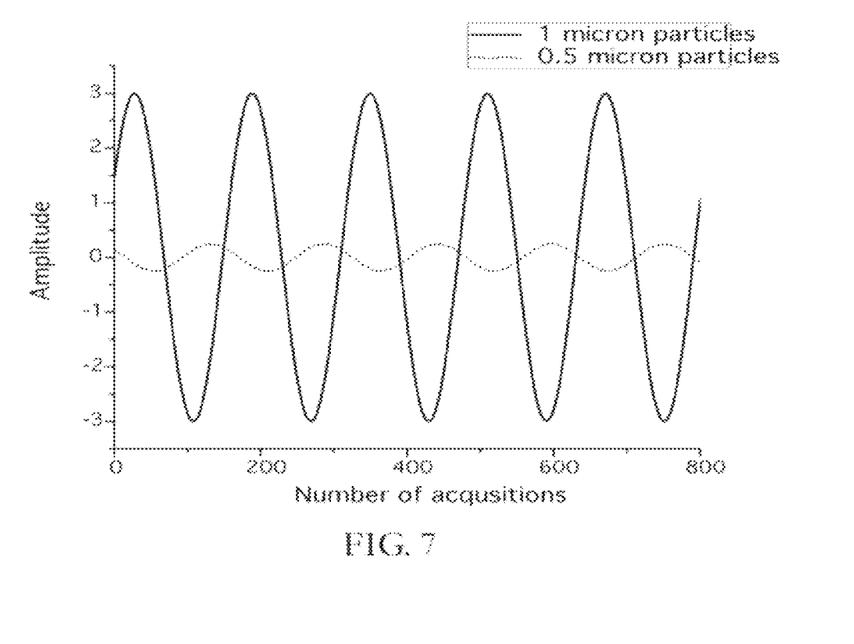
FIG. 7 shows an exemplary variation of an impedance of an electrode upon application of an oscillating magnetic field to a measurement chamber containing a suspension of magnetic indicator particles of 0.5 µm and 1.0 µm, according to some embodiments of the present invention.

FIG. 7 shows an exemplary sequence of steps performed by an embodiment of system 10 configured to detect the presence of and/or determine the concentration of a target analyte of substantially high molecular weight. In some embodiments, analytes of substantially high molecular weight comprise biological cells (e.g., bacteria), clusters of cells, and clusters of magnetic indicator particles, among others. In some embodiments, the method includes binding magnetic indicator particles to the surface of the analyte and measuring variations in the electrical and/or optical properties of the sensor surface, variations determined by the motion of the analyte particles under the effect of an oscillating magnetic field. The sequence of steps comprises:

a) Preparing a sample including the target analyte and indicator particles. In some embodiments, indicator particles 62 such as super-paramagnetic beads are functionalized by immobilizing affine compounds (e.g. antibodies or aptamers) on the surface of the indicator particles, the affine compounds chosen to determine a specific binding of the respective indicator particles to target analyte 60.

b) Incubating the sample with the functionalized indicator particles. In some embodiments, incubating allows indicator particles 62 to attach specifically to target analyte 60, forming analyte-indicator particle complexes and/or clusters. The size and type of indicator particle is chosen so that incubation leads to a maximum number of indicator particles attaching to the target analyte. Moreover, it may be desirable to use indicator particles which give a weak signal when not attached to the target analyte.

c) injecting the sample into the measurement chamber. In some embodiments, the incubated sample is concentrated before injection into measurement chamber 12. Beside analyte-indicator particle clusters, the sample may include a residual quantity of un-bound indicator particles; in some embodiments such un-bound particles are removed from the sample before injection into the measurement chamber. In some embodiments, un-bound particles may be removed from the sample using magnetic methods.

d) applying an oscillating stimulus such as an oscillating magnetic field to the sample, and performing a set of measurements of a physical property (e.g., electrical impedance and/or optical properties) of the sensor surface. In some embodiments, applying an oscillating magnetic field induces a motion and/or a deformation of the target analytes/indicator particles within the sample. The amplitude of the motion may depend on the size of the analyzed particles and/or on the parameters of the applied field (see e.g., FIG. 6). In some embodiments, the parameters of the oscillating field are chosen so as to maximize the motion of the analyzed particles. The size of analyzed particles may depend on the concentration of target analyte within the sample, and on the duration of incubation, among others.

In some embodiments, sample actuator 40 is controlled by control unit 34 to produce the oscillating field by e.g. moving a set of magnets with respect to measurement chamber 12, as described above. Other examples of oscillating stimuli which may determine a motion or a structural deformation of a constituent of the sample include optical, electrical, and mechanical actuation, among others.

Figure 8:
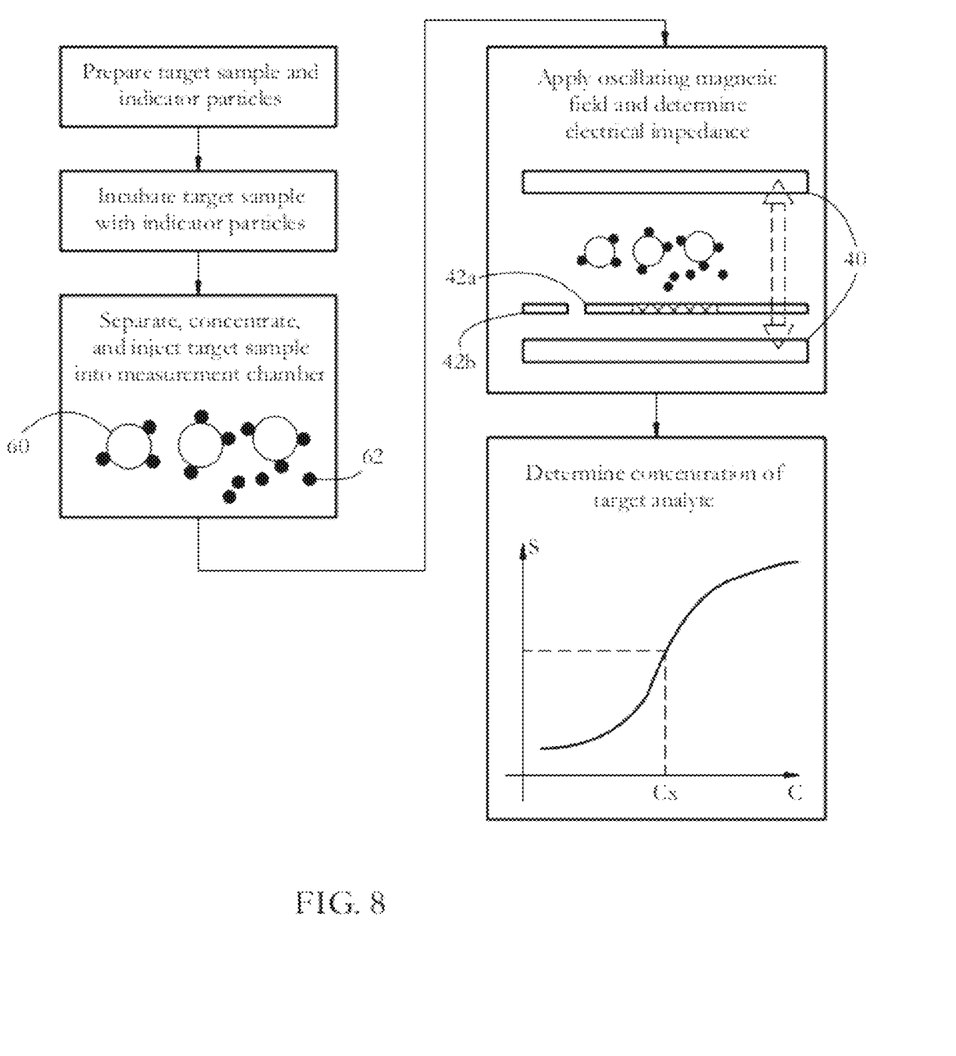
FIG. 8 shows an exemplary sequence of steps carried out to determine a concentration of a target analyte comprising biological cells, according to some embodiments of the present invention.

In some embodiments, impedance and/or optical signals are measured by EI analyzer 30 and/or optical analyzer 32, respectively, and are further processed to extract a frequency component of the signals at the frequency of the oscillating stimulus. The amplitude of said frequency component, as well as the phase shift between the measured signals and the applied stimulus, may be used to determine the concentration of the target analyte as illustrated below.

e) determining the concentration of the target analyte. In some embodiments, the concentration of the target analyte is calculated according to a calibration curve, by comparing the signals measured for the sample to signals measured for a set of reference samples containing known concentrations of target analyte. In some embodiments, to determine the calibration curve, a relative amplitude is determined by comparing the amplitude of the impedance measured for a reference sample containing a known concentration of target analyte to the amplitude of the impedance measured for a sample substantially free of the target analyte. An exemplary relative amplitude may be computed as follows:

$$A_{rel} = \frac{A_{cel}}{A_{ind}} - 1, \quad [1]$$

wherein $A_{cel}$ denotes the amplitude of the oscillation of the impedance at the frequency of the oscillating magnetic field, measured for a sample containing target analyte/indicator particle clusters, and wherein $A_{ind}$ denotes the amplitude of the oscillation of the impedance at the frequency of the oscillating magnetic field, measured for a reference sample containing a suspension of indicator particles, substantially free of target analyte. An exemplary set of calibration data is given in Table 1, for a target analyte comprising E. coli bacteria. An exemplary calibration curve is shown in FIG. 8.

TABLE 1

| E. coli concentration (cell/ml) | Relative amplitude | Standard deviation |
| --- | --- | --- |
| 0 | 0 | ±0.33 |
| $10^4$ | 4.89 | ±0.75 |
| $10^5$ | 13.00 | ±2.33 |
| $10^6$ | 23.72 | ±1.50 |

In some embodiments, after performing the measurement, chamber 12 is emptied of the sample using pump 16; the sample is removed to evacuation reservoir 18. Sample reservoir 14 may be replaced by a reservoir containing saline solution, which is pumped through measurement chamber 12 to flush the remaining target analyte. In some embodiments, optical measurement area 44 is monitored to determine whether the optical signal reverts to the level measured before injecting the sample, indicating that the measurement chamber is clean, and that another analysis is possible.

The following description provides an explicit example illustrating a method of determining the concentration of a high molecular weight target analyte: E. coli bacteria. The exemplary measurement comprised the following steps:

To prepare the indicator particles, a suspension of 500 nm super paramagnetic beads (e.g. MASTERBEADS® from ADEMTECH SA) in de-ionized water, with a concentration of $10^9$ particles/mL, was washed with a buffer solution of 2-(N-morpholino) ethanesulphonic acid (MES), at 50 mM and pH of 5.4. Next, a mix of 1-ethyl-3(3-dimethylaminopropyl) carbodiimide (EDC) and N-hydroxysuccinimide (NHS) was prepared at a ratio of 4:1 in MES. The MES buffer was replaced by the EDC/NHS mixture, and the suspension of indicator particles was agitated for 10 minutes at 37° C. and 1500 rpm. The suspension was then washed with distilled water and PBS buffer solution at pH 7.4, and then exposed to a solution of PBS containing anti-E. coli antibodies. The suspension was agitated for 2 hours at 37° C. and 1500 rpm (the step of protein immobilization), and then washed twice with PBS pH 7.4. The PBS solution was replaced with a solution of ethanolamine pH 8.5 to block any active sites on the indicator particles, that have not been bound to anti-E. coli antibodies. Then the sample was washed again, twice, with PBS pH 7.4.

To incubate the prepared indicator particles with the target analyte (*E. coli* bacteria), the suspension of indicator particles was subjected to ultrasound for 10 min. Then, a sample was prepared by adding 1 μL of indicator particle suspension to each 100 μL of bacterial suspension. The sample was agitated for 1 h at 7° C. and 1500 rpm, then washed with PBS buffer and injected into the measurement chamber.

In an embodiment using a sample actuator 40 comprising moving magnets, with the inferior magnet below the sensor and the superior magnet placed at the maximum distance away from the sensor, the sample was injected for 5 minutes at 25 μL/min, and then left undisturbed for 5 minutes for the signal to stabilize. Then the moving superior magnet was actuated at a frequency of 0.24 Hz and a range of motion of 22 mm, in a direction perpendicular to the sensor surface. Several measurement cycles were carried out, each consisting of 4200 determinations of the impedance of the electrode pair 42*a-b* at 500 kHz; the amplitude of the frequency component of the impedance at the actuating frequency of 0.24 Hz was calculated at $A_{cel}$=123.6±23.4 mV and compared to the amplitude determined for a reference sample containing only a suspension of indicator particles (magnetic beads, prepared as indicated above), $A_{ind}$=8.8±3.5 mV. A relative amplitude $A_{rel}$≈13 indicated a concentration of *E. coli* of $10^5$ cells/mL.

Figure 9:
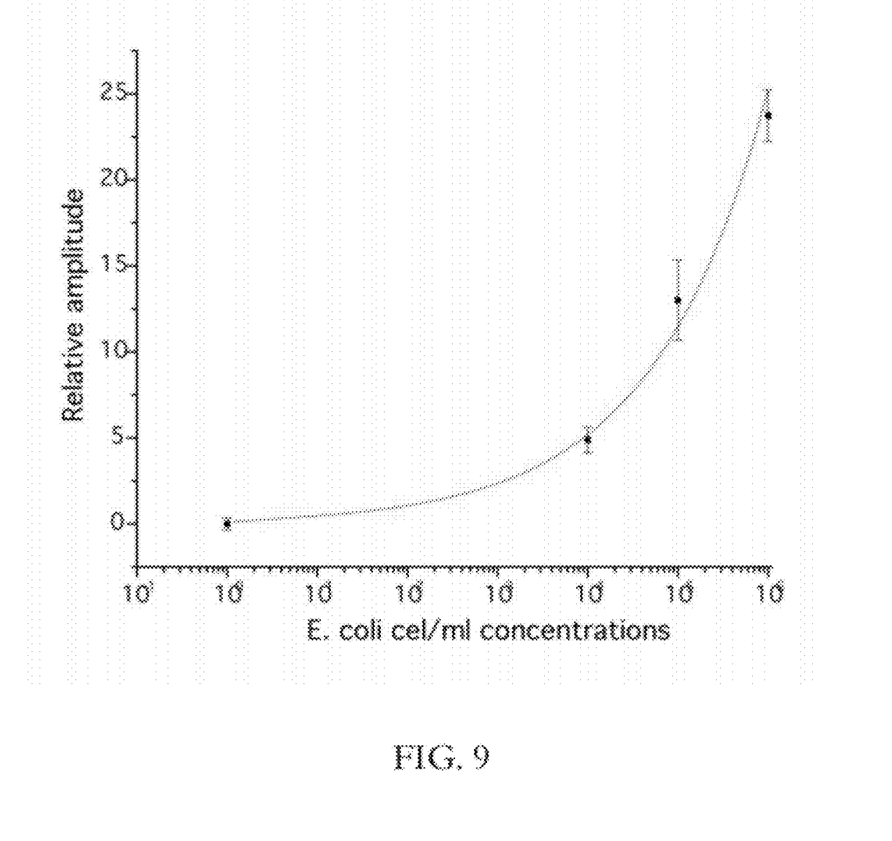
FIG. 9 illustrates an exemplary calibration curve for determining a concentration of *E. coli* bacteria according to some embodiments of the present invention.

FIG. 9 shows an exemplary sequence of steps performed by an embodiment of system 10 configured to detect the presence of and/or determine the concentration of a small target analyte. In some embodiments, small target analytes have a molecular weight substantially lower than a biological cell. Exemplary small target analytes include viruses, polypeptides, toxins, pesticides, drugs, drug residues, and low molecular weight compounds, among others. In some embodiments, the method includes functionalizing the surface of sensor 12 to allow the specific binding of target analytes to the sensor surface, functionalizing a set of indicator particles to allow the indicator particles to bind to the sensor surface, and measuring variations in the electrical and/or optical properties of the sensor surface, variations determined by the motion and/or deformation of indicator particles bound to the sensor surface produced by the application of an oscillating stimulus such as an oscillating magnetic field. The sequence of steps comprises:

a) preparing the sample and indicator particles. In some embodiments, a set of indicator particles 162 are functionalized by immobilizing on the surface of the indicator particles a set of linkers, the distal end of each linker having an affine structure similar to those present on the target analyte. Such linkers may allow the indicator particles to attach in a non-rigid manner (e.g., to oscillate) to active sites on the surface of the sensor, active sites configured to bind target analytes as described below.

b) preparing the sensor surface. In some embodiments, the surface of sensor 20 is functionalized by immobilizing on the sensor surface a set of active sites susceptible to selectively bind to the target analyte. An exemplary active site comprises an affine partner of the target analyte.

c) injecting the sample into measurement chamber 12. In some embodiments, introducing a target analyte 160 into measurement chamber 12 may result in affine binding of the target analyte to the active sites of sensor 20, functionalized as described above. A certain fraction of active sites are thus occupied, according to the concentration of the target analyte.

d) injecting the functionalized indicator particles into the measurement chamber. Having attached an affine partner of an active site on the sensor surface, the indicator particles may bind via the linker to any active sites not occupied by target analytes. In some embodiments, the concentration of indicator particles is sufficiently high, to ensure a complete occupation of the empty active sites of sensor 20, even when the sample is substantially free of target analytes.

e) applying an oscillating stimulus, e.g. an oscillating magnetic field, to measurement chamber 12, and measuring the variation of a physical parameter (e.g., impedance or optical properties) of sensor 20, variation induced by a motion and/or deformation of the indicator particles bound to the surface of sensor 20 caused by the application of the oscillating stimulus. In some embodiments, a frequency component of the measured signal at a frequency equal to the frequency of the applied stimulus is extracted. The amplitude of said frequency component, as well as the phase shift between the measured signals and the applied stimulus, may be used to determine the concentration of the target analyte.

f) determining the concentration of the target analyte. In some embodiments, the concentration of the target analyte is calculated according to a calibration curve, e.g. by comparing the signals measured for the sample to signals measured for a set of reference samples containing known concentrations of target analyte. In some embodiments, a signal produced by a sample with high target analyte concentration may be weaker than signal produced by a sample with lower concentration of target analyte, since the method monitors the motion/deformation of indicator particles which occupy active sites on the sensor left unoccupied by target analytes; the higher the target analyte concentration, the fewer the active sites left unoccupied during the sample injection stage.

Figure 10:
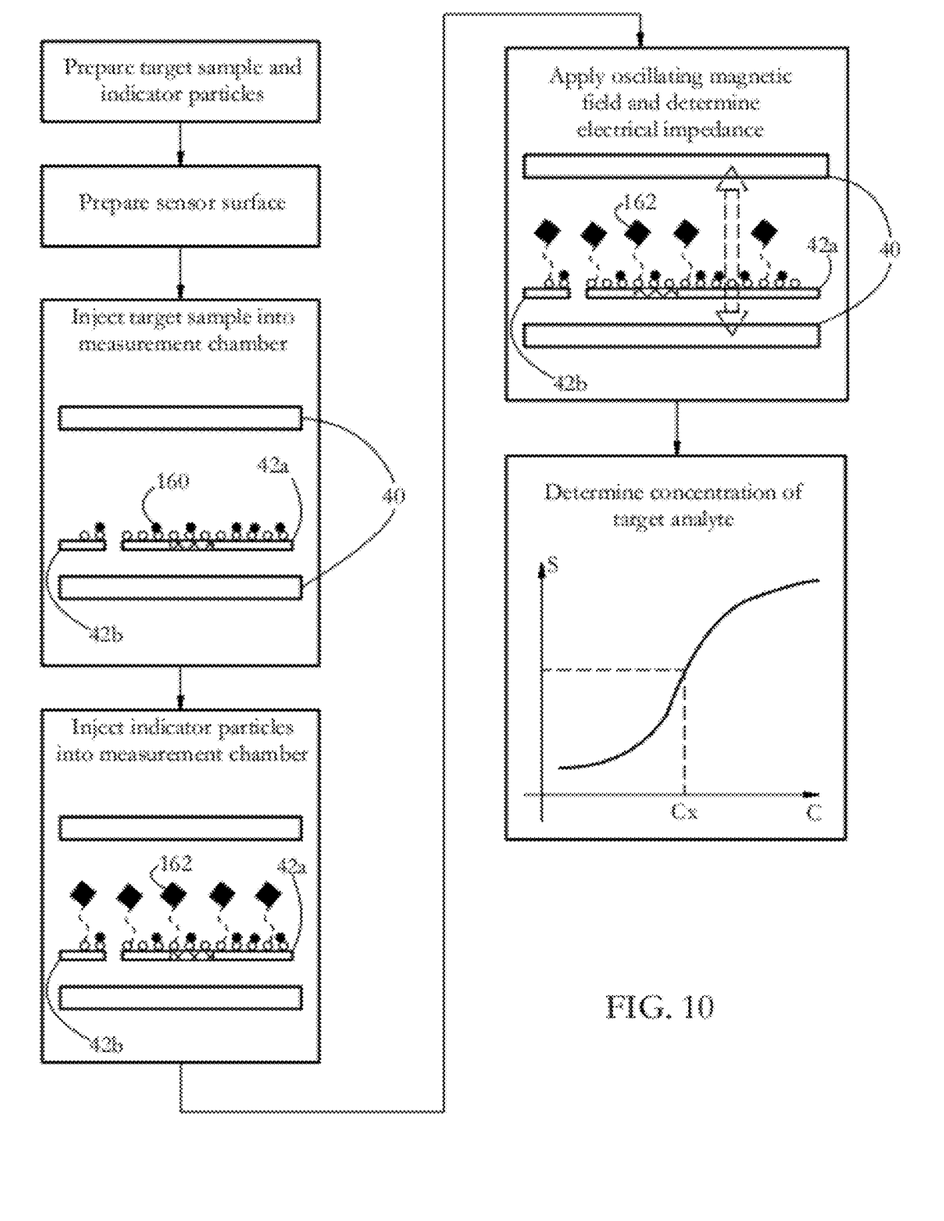
FIG. 10 shows an exemplary sequence of steps carried out to determine a concentration of an analyte of low molecular weight, according to some embodiments of the present invention.
Figure 11:
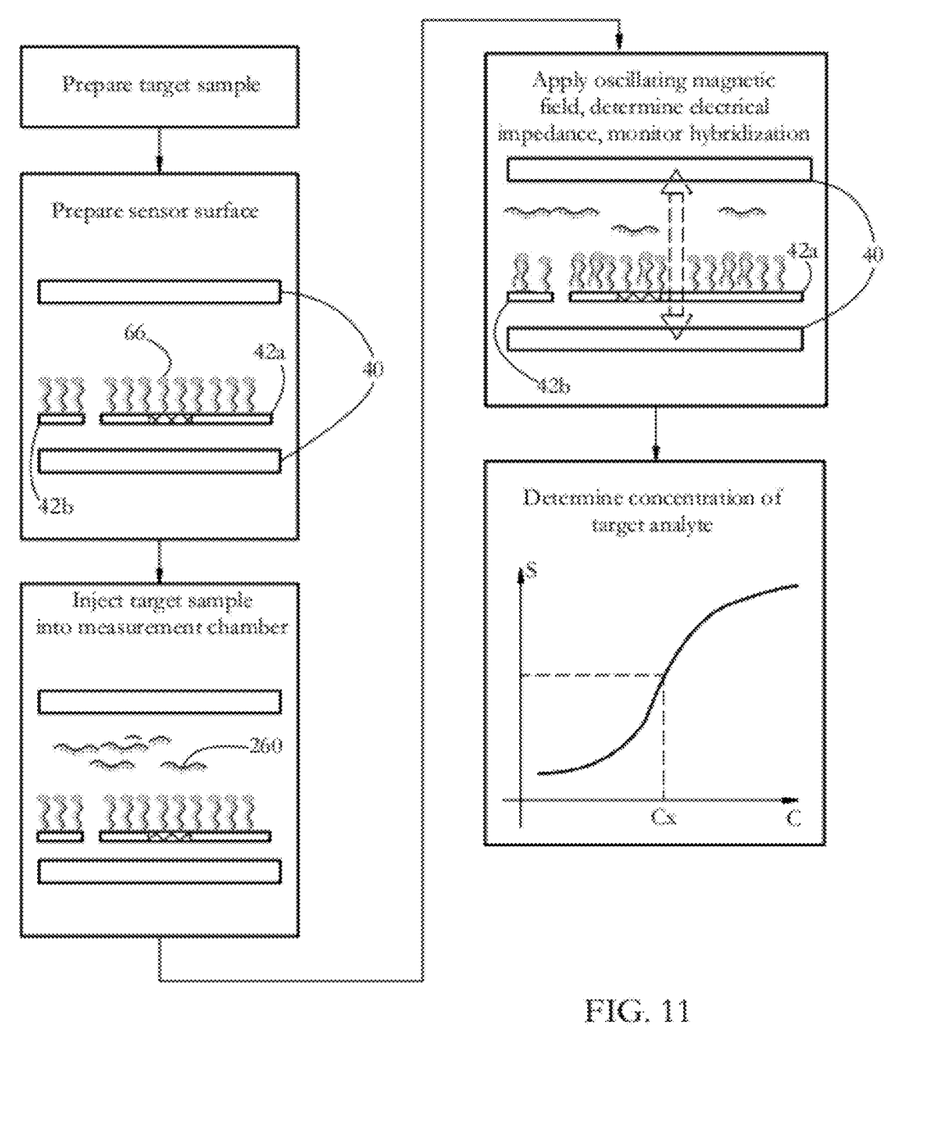
FIG. 11 shows an exemplary sequence of steps carried out to determine a concentration of an analyte comprising a DNA strand, according to some embodiments of the present invention.

FIG. 10 shows an exemplary sequence of steps performed by an embodiment of system 10 configured to detect the presence of and/or determine the concentration of a target analyte comprising a DNA strand. In some embodiments, the method includes monitoring a hybridization of the target DNA strand. The sequence of steps comprises:

a) preparing the sensor surface. In some embodiments, the surface of sensor 20 is functionalized to immobilize one end of a complementary DNA strand 66, wherein strand 66 is complementary to the target DNA strand. Such complementary DNA strands 66 are further functionalized to attach an indicator particle (e.g. a magnetic bead) to the free end of each strand.

b) preparing the sample. In some embodiments, the sample containing a target DNA strand 260 is prepared in liquid form.

c) injecting the sample into measurement chamber 12.

d) employing sample actuator 40 to apply an oscillating stimulus, e.g., an oscillating magnetic field to measurement chamber 12. The properties of the applied field, such as intensity, and frequency of oscillation, may be chosen by a user according to certain features of the target analyte. In some embodiments, applying the oscillating field produces a variation in the position of the indicator particle attached to target DNA strand 260. Such variation may induce measurable variations of a physical property, e.g., impedance and/or index of refraction of the sample in the vicinity of sensor 20.

In some embodiments, EI analyzer 30 and/or optical analyzer 32 are used to determine a variation of a measured signal, variation induced by a displacement and/or change of shape of complementary DNA strands 66 attached to the indicator particles as described above. In some embodiments, impedance and/or optical measurements may be used to monitor a process of DNA hybridization taking place within the measurement chamber. Hybridization comprises a specific binding of target DNA strand 260 to complementary DNA strand 66. In some embodiments, as described above, complementary DNA strand 66 has one end attached to sensor 20, while the other end is attached to an indicator particle such as a paramagnetic bead, which may oscillate under the influence of the oscillating field supplied by sample actuator 40. Differences in rigidity between double-strand DNA (obtained as a result of the hybridization process) and single strand DNA (such as complementary DNA strand 260) may produce a measurable alteration of the amplitude and/or phase of an oscillation of an indicator particle actuated by the oscillating field. In some embodiments, the progress of DNA hybridization is accompanied by a reduction in the amplitude of oscillation of indicator particles, due to a progressive stiffening of the DNA complex. Therefore the progress of DNA hybridization may be revealed by a decrease in an oscillation of a physical property (e.g., impedance) of the sample in the vicinity of sensor 20, measured by EI analyzer 30 and/or optical analyzer 32. In some embodiments, a frequency component of the measured signal at a frequency equal to the frequency of the applied stimulus is extracted. The amplitude of said frequency component, as well as the phase shift between the measured signals and the applied stimulus, may be used to monitor the DNA hybridization process.

e) determine the concentration of the target analyte. In some embodiments, the concentration of target DNA strands 260 is calculated according to a calibration curve, by comparing the signals measured for the sample to signals measured for a set of reference samples containing known concentrations of target analyte. In some embodiments, the concentration of target analyte may be further determined according to parameters of the dynamics of the DNA hybridization process determined as described above, and/or according to an amplitude and/or phase of a measured signal determined at a stationary level of hybridization, e.g. at the completion of the DNA hybridization process.

Figure 12:
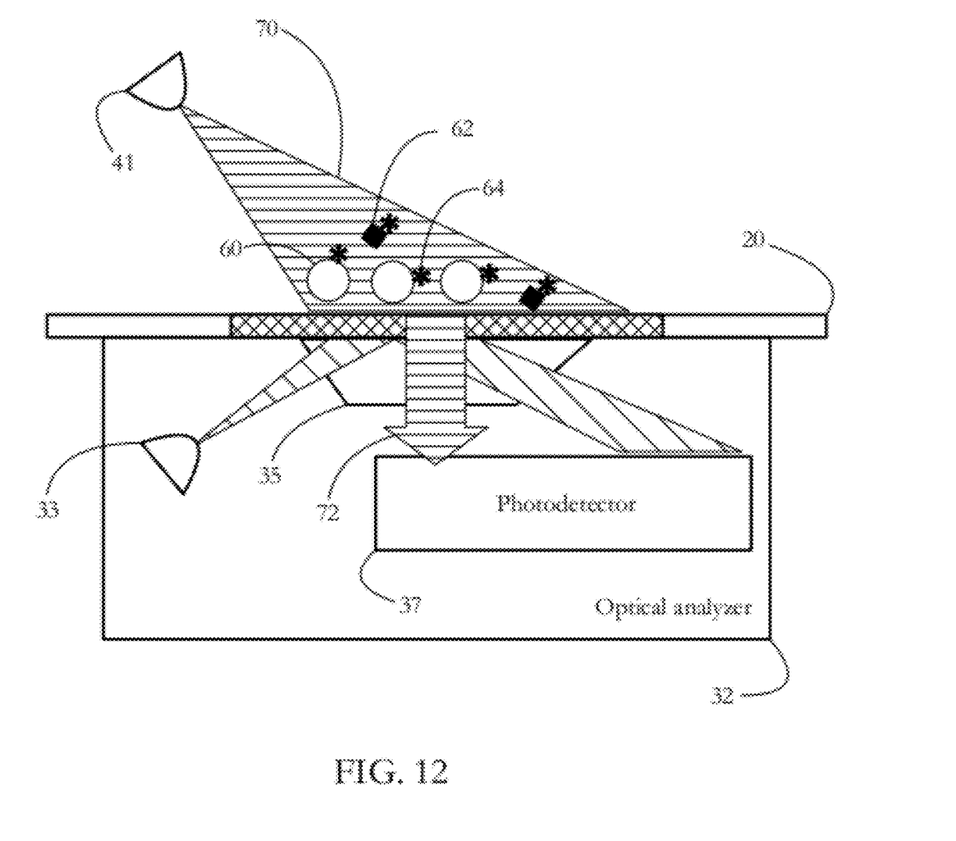
FIG. 12 illustrates an exemplary system for applying an optical actuation to the sample and measuring an effect of the optical actuation, according to some embodiments of the present invention.

In some embodiments, detection of certain analytes (e.g. ochratoxin and aflatoxin found in food, or orelanine found in toxic mushrooms) may be performed using optical actuation of the sample. FIG. 12 shows an exemplary system for applying an optical actuation to the sample and determining the concentration of a target analyte according to an effect of the optical actuation. In some embodiments, target analyte 60 is inherently florescent, or may be prepared to fluoresce by attaching a fluorescent marker 64, such as a fluorescent chromophore, to target analyte 60. In some embodiments, fluorescent marker 64 may be attached to an indicator particle. In some embodiments, an optical actuator 41 comprises a light source producing an actuation beam 70 configured to illuminate the sample. The frequency of the light emitted by actuator 41 may be chosen to induce fluorescence of target analyte 60 and/or of indicator particles 62. The position of actuator 41 with respect to sensor 20 and/or optical analyzer 32 is not limited to the example of FIG. 12. In some embodiments, actuator 41 may form part of sample actuator 40, or part of optical analyzer 32. For example, actuator 41 may be incorporated with light source 33 of optical analyzer 32.

In some embodiments, actuator 41 is configured to emit light of stationary intensity. In some embodiments, the intensity of light emitted by actuator 41 may oscillate with an actuation frequency, which may be adjustable. In an exemplary method employing optical actuation, the sample is illuminated with an actuation beam 70 of oscillating intensity. Actuation beam 70 may induce a fluorescence 72 in the sample comprising fluorescent analytes and/or indicator particles. Photodetector 37 may be employed to determine the intensity of fluorescent beam 72 emitted by the sample. The intensity of fluorescent beam 72 may oscillate due to oscillations in the intensity of actuation beam 70 and/or due to an oscillation of target analyte 60 and/or indicator particles 62 induced by an applied oscillating magnetic field to the measurement chamber, as described above. In some embodiments, control system 34 may be configured to compute a frequency component of the intensity of fluorescent beam 72 at the actuation frequency, and to determine the concentration of target analyte 60 according to an amplitude and/or a phase of the frequency component, e.g. by employing calibration curves.

The exemplary systems and methods described above allow the detection of, and determination of a concentration of a target analyte such as bacteria, viruses, and DNA strands, among others, in a fluid sample. To determine the concentration of the target analyte, some embodiments of the present invention apply a variable physical stimulus, such as an oscillating magnetic field, to a sample containing the target analyte. The physical stimulus produces changes in a physical property, such as a position, a shape, or a chemical structure, of a constituent of the sample, changes which may further determine measurable variations of a physical property, such as an impedance or an index of refraction, of a sensor surface. Such variations may be measured using e.g. electrical impedance or surface plasmon resonance analyzers, to determine the concentration of the target analyte. For example, some methods and systems described here utilize an amplitude and/or a phase of oscillation of an electrical quantity, such as the real or imaginary part of the electrical impedance of an electrode pair, oscillation induced by the application of an oscillating magnetic field, to determine the concentration of the target analyte. Similarly, the concentration of the target analyte may be determined according to variations of an optical property such as the refractive index of the sensor, produced by an oscillating magnetic field.

In some embodiments, the oscillating stimulus induces oscillations of a selected constituent of the sample. Such selected constituents include:

target analytes such as biological cells, which may be attached to indicator particles (e.g. magnetic beads); indicator particles have an active role in the motion of the target analyte and/or in increasing the amplitude of the oscillation of the measured signal;

indicator particles attached to the sensor surface at a collection of active sites configured to specifically bind a target analyte of low molecular weight, such as a virus or polipeptide.

indicator particles attached to a DNA strand complementary to a target DNA strand of a target analyte.

In some embodiments of the present invention, indicator particles such as magnetic beads are bound to either the target analyte or to the sensor, producing a substantial amplification of the measured signal compared to a situation in which no indicator particles are used.

While conventional analytic methods using impedance or optical measurements to detect target analytes have a limited sensitivity, some embodiments of the present invention may substantially improve sensitivity, potentially by orders of magnitude, by using the applied oscillating stimulus to amplify the measured signal. This enhancement in sensitivity may reduce the need for additional steps of sample preparation, such as sample concentration and/or incubation, required in conventional methods. Such additional steps are typically costly, comprising the use of expensive reactants and specialized equipment, and are often time consuming; for example, in the case of pathogens, biological cultivation often exceeds 24 hours.

Conventional methods typically employ analyte-specific sensors; such sensors are often functionalized to bind a specific type of analyte in order to determine its concentration. In some embodiments of the present invention, sensors are passivated to prevent adsorption of the target analyte. Since some of the described methods do not require the target analyte to bind to the sensor, the same sensor may be used for the detection of a wide range of analytes.

In conventional analytic methods, an optical measurement area of an optical analyzer and an electrode pair of an impedance analyzer are spatially separated, even when placed on a common sensor. In some embodiments of the present invention, an optical measurement area and an impedance electrode have a substantial overlap, which allows a simultaneous determination of optical and electric properties of the same area of the sensor. In some embodiments, a loss of sensitivity, e.g. of the impedance analyzer due to such overlap, may be compensated by an amplification of the measured signal due to using indicator particles and the application of the oscillating stimulus.

When applied to a sample comprising a DNA fragment, some embodiments of the present invention allow not only determining a concentration of the target analyte, but also monitoring and/or influencing a DNA hybridization process. By attaching a magnetic bead to one end of a DNA fragment and immobilizing the other end of the DNA fragment on the sensor surface, the respective strand may be stretched in a controlled fashion by the application of an actuating magnetic field, without having to resort to support structures, as in some conventional methods for monitoring hybridization. The parameters of the actuating field, such as intensity, gradient, waveform, and frequency may be chosen so as to influence the yield of hybridization.

It will be clear to one skilled in the art that the above embodiments may be altered in many ways without departing from the scope of the invention. Accordingly, the scope of the invention should be determined by the following claims and their legal equivalents.

What is claimed is:

1. A method comprising:
    employing a magnet to apply an oscillating actuating magnetic field to a sample contained in a measurement chamber so as to induce a motion and/or a deformation of a target analyte contained within the sample, the measurement chamber including an electrode pair, the applied actuating magnetic field oscillating with an actuation frequency;
    measuring an oscillation of an electrical impedance of the electrode pair, the oscillation of the electrical impedance produced in response to applying the actuating magnetic field, wherein measuring the oscillation of the electrical impedance comprises applying an electrical signal to the electrode pair, the electrical signal oscillating with a measuring frequency distinct from the actuating frequency;
    and
    determining a concentration of the target analyte in the sample according to the oscillation of the electrical impedance.

2. The method of claim 1, wherein the target analyte is attached to a magnetic bead.

3. The method of claim 1, wherein an electrode of the electrode pair is passivated with respect to the target analyte.

4. The method of claim 1, wherein the target analyte comprises a first DNA strand, and wherein the method further comprises, in preparation for applying the actuating magnetic field:
    receiving in the measurement chamber a second DNA strand complementary to the first DNA strand, the second DNA strand being attached to a magnetic bead; and
    attaching the second DNA strand to a selected electrode of the electrode pair.

5. The method of claim 4, further comprising determining a degree of hybridization of the first and second DNA strands according to the oscillation of the electrical impedance.

6. The method of claim 4, further comprising adjusting the first frequency in order to increase a yield of a hybridization of the first and second DNA strands.

7. The method of claim 1, further comprising:
    measuring an index of refraction of a layer of the sample in contact to at least an electrode of the electrode pair, the index of refraction being indicative of the motion and/or deformation of the target analyte in response to applying the actuating magnetic field; and
    determining the concentration of the target analyte in the sample further according to the index of refraction.

8. The method of claim 1, further comprising:
    illuminating the sample with an actuating light beam to induce a fluorescence of the target analyte or a fluorescence of a fluorescent marker attached to the target analyte;
    measuring an oscillation of an intensity of the fluorescence, the oscillation of the intensity of the fluorescence produced in response to applying the actuating magnetic field; and
    determining the concentration of the target analyte in the sample further according to the oscillation of the intensity of the fluorescence.

9. A system comprising:
    an electrode pair in contact to a sample comprising a target analyte;
    a magnet configured to apply an oscillating actuating magnetic field to the sample, the actuating magnetic field oscillating with an actuation frequency;
    an electrical impedance analyzer configured to measure an oscillation of an electrical impedance of the electrode pair, the oscillation of the electrical impedance indicative of a motion and/or deformation of the target analyte, the motion and/or deformation induced in response to applying the actuating magnetic field, wherein measuring the oscillation of the electrical impedance comprises applying an electrical signal to the electrode pair the electrical Signal oscillating with a measuring frequency distinct from the actuating frequency; and
    a measurement system configured to
    determine a concentration of the target analyte in the sample according to the oscillation of the electrical impedance.

10. The system of claim 9, wherein the target analyte is attached to a magnetic bead.

11. The system of claim 9, wherein an electrode of the electrode pair is passivated with respect to the target analyte.

12. The system of claim 9, wherein the target analyte comprises a first DNA strand, and wherein the sample comprises a second DNA strand complementary to the first DNA strand, the second DNA strand being attached to a magnetic bead and to a selected electrode of the electrode pair.

13. The system of claim 12, wherein the measurement system is further configured to determine a degree of hybridization of the first and second DNA strands according to the oscillation of the electrical impedance.

14. The system of claim 12, wherein the measurement system is further configured to adjust the first frequency in order to increase a yield of a hybridization of the first and second DNA strands.

15. The system of claim 9, further comprising an optical analyzer configured to determine an oscillation of an index of refraction of a layer of the sample in contact to at least an electrode of the electrode pair, the oscillation of the index of refraction indicative of the motion and/or deformation of the target analyte induced in response to applying the oscillating actuating magnetic field, and wherein the measurement system is configured to determine the concentration of the target analyte in the sample further according to the oscillation of the index of refraction.

16. The system of claim 9, further comprising an actuating light source configured to illuminate the sample with an actuating light beam to induce a fluorescence of the target analyte or a fluorescence of a fluorescent marker attached to the target analyte, and wherein the measurement system is further configured to:

measure an oscillation of an intensity of the fluorescence, the oscillation of the intensity of the fluorescence produced in response to applying the actuating magnetic field; and     determine the concentration of the target analyte in the sample further according to the oscillation of the intensity of the fluorescence.

17. A method comprising:

bringing into contact an electrode pair with a first sample comprising a target analyte, wherein a selected electrode of the electrode pair comprises a set of active sites configured to bind to the target analyte;

in response to bringing into contact the electrode pair with the first sample, bringing into contact the electrode pair with a second sample comprising a set of magnetic beads configured to bind to the active sites;

employing a magnet to apply an oscillating actuating magnetic field to the electrode pair so as to induce a motion and/or a deformation of a subset of the set of magnetic beads, wherein each bead of the subset is bound to an active site of the set of active sites, and wherein the actuating magnetic field oscillates with an actuation frequency;

measuring an oscillation of an electrical impedance of the electrode pair, the oscillation of the electrical impedance indicative of the motion and/or deformation of the subset of the set of magnetic beads in response to applying the actuating magnetic field, and wherein measuring the oscillation of the electrical impedance comprises applying an electrical signal to the electrode pair, the electrical signal oscillating with a measuring frequency distinct from the actuating frequency;

and determining a concentration of the target analyte in the sample according to the oscillation of the electrical impedance.

18. A method comprising:

employing a magnet to apply an oscillating actuating magnetic field to a sample comprising a target analyte so as to induce a motion and/or a deformation of the target analyte, the applied actuating magnetic field oscillating with an actuation frequency;

illuminating the sample with a light beam;

employing a photodetector to determine an oscillation of an intensity of light received from the sample in response to illuminating the sample, the oscillation of the intensity of light occurring in response to applying the actuating magnetic field;

and determining a concentration of the target analyte in the sample according to the oscillation of the intensity of light.

19. The method of claim 5, further comprising adjusting the first frequency in order to increase a yield of a hybridization of the first and second DNA strands.

20. The system of claim 13, wherein the measurement system is further configured to adjust the first frequency in order to increase a yield of a hybridization of the first and second DNA strands.

21. The method of claim 1, wherein determining the concentration of the target analyte comprises determining a frequency domain representation of the oscillation of the electrical impedance, the frequency domain representation comprising a frequency component oscillating with the actuation frequency, and wherein the concentration of the target analyte is determined according to the frequency component.

22. The system of claim 9, wherein the measurement system is configured to determine the concentration of the target analyte according to a frequency component of the oscillation of the electrical impedance, the frequency component oscillating with the actuation frequency, the frequency component forming a part of a frequency domain representation of the oscillation of the electrical impedance.

* * * * *